United States Patent [19]

Heine et al.

[11] Patent Number: 5,326,771

[45] Date of Patent: Jul. 5, 1994

[54] PIPERIDYLMETHYL-SUBSTITUTED CHROMAN DERIVATIVES

[75] Inventors: Hans-Georg Heine, Krefeld; Bodo Junge, Wuppertal; Peter-Rudolf Seidel, Cologne; Rudolf Schohe-Loop, Wuppertal; Thomas Glaser, Overath; Jean M. V. De Vry, Roesrath; Wolfgang Dompert; Henning Sommermeyer, both of Cologne, all of Fed. Rep. of Germany

[73] Assignee: Bayer Aktiengesellschaft, Leverkusen, Fed. Rep. of Germany

[21] Appl. No.: 983,988

[22] Filed: Nov. 30, 1992

[30] Foreign Application Priority Data

Dec. 9, 1991 [DE] Fed. Rep. of Germany ....... 4140542

[51] Int. Cl.$^5$ ................. A61K 31/445; C07D 405/06; C07D 405/14
[52] U.S. Cl. .................... 514/316; 514/320; 546/187; 546/196; 546/206
[58] Field of Search ........ 546/187, 196, 206; 514/316, 320

[56] References Cited

U.S. PATENT DOCUMENTS

| 3,759,927 | 9/1973 | Huebner | 260/293.58 |
| 3,826,835 | 7/1974 | Huebner | 424/267 |
| 3,845,060 | 10/1974 | Huebner | 260/293.58 |
| 4,376,123 | 3/1983 | Hausberg et al. | 546/196 |
| 4,745,114 | 5/1988 | Elliott et al. | 546/196 |
| 4,957,928 | 9/1990 | Frostl et al. | 514/318 |
| 5,112,855 | 5/1992 | Frostl et al. | 514/456 |
| 5,137,901 | 8/1992 | Junge et al. | 514/373 |

FOREIGN PATENT DOCUMENTS

| 2165276 | 7/1972 | Fed. Rep. of Germany . |
| 3620408 | 12/1986 | Fed. Rep. of Germany . |
| 2583266 | 12/1986 | France . |

OTHER PUBLICATIONS

J. Med. Chem. 22 (6) 539–544, 1986.
Eur. J. Med. Chem. 22 (6) 539–544, 1987.
Farmaco, Ed. Sci. 42 (11) 805–813, 1989.
Aldrichimica Acta 18, 25, 1985.
Still et al, J. Org. Chem. 43, 2923, 1978.

Primary Examiner—Marianne M. Cintins
Assistant Examiner—Phyllis Spivack
Attorney, Agent, or Firm—Sprung Horn Kramer & Woods

[57] ABSTRACT

Piperidylmethyl-substituted chroman derivatives can be prepared by first reducing corresponding chroman-carboxylic acid derivatives, if appropriate with prior activation, with the cyclic amines and then reducing the carbonyl group, or by reacting chromanmethyl compounds directly with the cyclic amines. The substituted piperidylmethyl-substituted chroman derivatives can be employed as active compounds in medicaments, in particular for the treatment of diseases of the central-nervous system.

15 Claims, No Drawings

PIPERIDYLMETHYL-SUBSTITUTED CHROMAN DERIVATIVES

The invention relates to piperidylmethyl-substituted chroman derivatives, processes for their preparation and their use in medicaments, in particular as agents for combating diseases of the central nervous system.

It is already known that 2-benzofuranylmethyl derivatives have an activity on the central nervous system (compare DE 2,165,276).

The compound 1-[(3,4-dihydro-2H-1-benzopyran-2-yl)methyl]piperidine in the form of its hydrochloride, having an α-adrenergic blocking action, is moreover described in the publication Eur. J. Med. Chem. 22 (6), 539–544.

The invention now relates to piperidylmethyl-substituted chroman derivatives of the general formula (I)

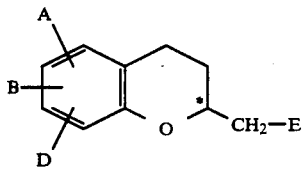

(I)

in which

A, B and D are identical or different and represent hydrogen, halogen, cyano, azido, nitro, difluoromethyl, trifluoromethyl, difluoromethoxy, trifluoromethoxy, hydroxyl or carboxyl, or represent straight-chain or branched alkyl, alkenyl, acyl or alkoxycarbonyl having in each case up to 8 carbon atoms, or represent a group of the formula $-NR^1R^2$, $-NR^3-L-R^4$ or $-OR^5$, wherein $R^1$, $R^2$ and $R^3$, are identical or different and denote hydrogen, straight-chain or branched alkyl having up to 8 carbon atoms, phenyl or benzyl, L denotes the $-CO-$ or $-SO_2-$ group, $R^4$ denotes straight-chain or branched alkyl having up to 8 carbon atoms or benzyl, or aryl having 6 to 10 carbon atoms, which is optionally substituted by halogen, hydroxyl, nitro, cyano, trifluoromethyl, trifluoromethoxy or by straight-chain or branched alkyl or alkoxy having up to 6 carbon atoms, $R^5$ denotes straight-chain or branched alkyl or alkenyl having in each case up to 8 carbon atoms, which are optionally substituted by cycloalkyl having 3 to 6 carbon atoms or phenyl, or A has one of the abovementioned meanings, and B and D together form a 5- to 7-membered saturated, partly unsaturated or aromatic carbocyclic radical or heterocyclic radical having up to 2 hetero atoms from the series comprising S, N and 0, wherein these can optionally have up to 2 carbonyl functions in the ring and are optionally substituted by up to 2 identical or different substituents from the group comprising straight-chain or branched alkyl, alkenyl and alkoxy having in each case up to 6 carbon atoms, hydroxyl, cycloalkyl having 3 to 6 carbon atoms, phenyl, halogen, cyano, nitro and, in spiro form, a radical of the formula

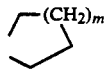

wherein m denotes the number 1 or 2,

E represents a heterocyclic radical of the formula

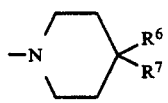

wherein $R^6$ denotes hydrogen, hydroxyl, halogen, phenyl or piperidinyl, $R^7$ denotes straight-chain or branched alkyl having up to 8 carbon atoms, which is optionally substituted by up to 3 identical or different substituents from the group comprising hydroxyl, straight-chain or branched alkoxy having up to 6 carbon atoms and phenyl, wherein the phenyl ring in turn can be substituted by up to 3 identical or different substituents from the group comprising halogen, trifluoromethyl, trifluoromethoxy and cyano, or denotes phenyl, which is optionally substituted by up to 3 identical or different substituents from the group comprising halogen, trifluoromethyl, trifluoromethoxy, cyano, nitro, hydroxyl and straight-chain or branched alkyl and alkoxy having in each case up to 6 carbon atoms, or denotes a group of the formula $-CO-NR^8R^9$, $-CO-R^{10}$ or $-OR^{11}$, wherein $R^8$ and $R^9$ are identical or different and denote hydrogen, straight-chain or branched alkyl having up to 6 carbon atoms or phenyl, and $R^{10}$ and $R^{11}$ are identical or different and denote phenyl, which is optionally substituted by up to 2 identical or different substituents from the group comprising halogen, cyano, nitro, trifluoromethyl and trifluoromethoxy, and salts thereof, with the proviso that $R^e$ does not denote hydrogen or hydroxyl if $R^7$ represents unsubstituted phenyl.

Physiologically acceptable salts are preferred in the context of the present invention. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

A heterocyclic radical in general represents a 5- to 7-membered, preferably 5- or 6-membered, saturated or unsaturated ring which can contain, as hetero atoms, up to 2 oxygen, sulphur and/or nitrogen atoms. 5- and 6-membered rings having one oxygen or sulphur atom and/or one or 2 nitrogen atoms are preferred. Rings which may be mentioned as preferred are: thienyl, furyl, pyrrolyl, pyrazolyl, pyranyl, pyridyl, pyrimidyl, pyrazinyl, pyridazinyl, thiazolyl, oxazolyl, imidazolyl, isoxazolyl, pyrrolidinyl, piperidinyl, piperazinyl, tetrazolyl, morpholinyl and dioxanyl.

The compounds according to the invention can be present in various stereoisomeric forms in the context of the present invention. The compounds according to the invention exist in stereoisomeric forms which either behave as mirror images (enantiomers), or do not behave as mirror images (diastereomers). The invention relates both to the antipodes and to the racemic forms, as well as to the diastereomer mixtures. The racemic forms, like the diastereomers, can be separated into the stereoisomerically uniform constituents in a known manner [compare E. L. Eliel, Stereochemistry of Carbon Compounds, McGraw Hill, 1962].

Preferred compounds of the general formula (I) are those in which

A, B and D are identical or different and represent hydrogen, fluorine, chlorine, bromine, cyano, trifluoromethyl, difluoromethoxy, trifluoromethoxy or hydroxyl, or represent straight-chain or branched alkyl, alkenyl, acyl or alkoxycarbonyl having in each case up to 6 carbon atoms, or represent a group of the formula —NR¹R², —NR³—L—R⁴ or —OR⁵, wherein R¹, R2 and R³, are identical or different and denote hydrogen or straight-chain or branched alkyl having up to 6 carbon atoms, L denotes the —CO— or —SO₂— group, R⁴ denotes straight-chain or branched alkyl having up to 6 carbon atoms or benzyl, or denotes phenyl, which is optionally substituted by fluorine, chlorine, bromine, trifluoromethyl, trifluoromethoxy or hydroxyl, or by straight-chain or branched alkyl or alkoxy having in each case up to 4 carbon atoms, R⁵ denotes straight-chain or branched alkyl or alkenyl having up to 6 carbon atoms, which are optionally substituted by cyclopropyl, cyclopentyl, cyclohexyl or phenyl, or A has one of the abovementioned meanings, and B and D together form a radical of the formula

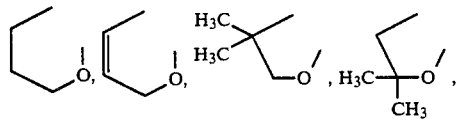

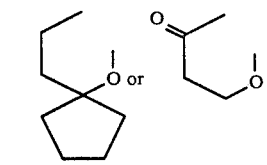

E represents a heterocyclic radical of the formula

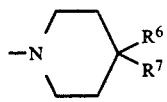

R⁶ denotes hydrogen, hydroxyl, fluorine, chlorine, bromine, phenyl or piperidinyl, R⁷ denotes straight-chain or branched alkyl having up to 6 carbon atoms, which is optionally substituted by up to 3 identical or different substituents from the group comprising hydroxyl, straight-chain or branched alkoxy having up to 4 carbon atoms and phenyl, wherein the phenyl ring in turn can be substituted by up to 3 identical or different substituents from the group comprising fluorine, chlorine, bromine and trifluoromethyl, or denotes phenyl, which is optionally substituted by up to 3 identical or different substituents from the group comprising fluorine, chlorine, bromine, trifluoromethyl, hydroxyl and straight-chain or branched alkyl and alkoxy having in each case up to 4 carbon atoms, or denotes a group of the formula —CO—NR⁸R⁹, —COR¹⁰ or —OR¹¹, wherein R⁸ and R⁹ are identical or different and denote hydrogen or straight-chain or branched alkyl having up to 4 carbon atoms, and R¹⁰ and R¹¹ are identical or different and denote phenyl, which is optionally substituted by up to 2 identical or different substituents from the group comprising fluorine, chlorine, bromine and trifluoromethyl, and salts thereof, with the proviso that R⁶ does not denote hydrogen or hydroxyl if R⁷ represents unsubstituted phenyl.

Particularly preferred compounds of the general formula (I) are those in which

A, B and D are identical or different and represent hydrogen, fluorine, chlorine, bromine, cyano, trifluoromethyl, trifluoromethoxy or hydroxyl, or represent straight-chain or branched alkyl or alkenyl having in each case up to 4 carbon atoms, or represent a group of the formula —NR¹R² or —OR⁵, wherein R¹ and R² are identical or different and denote hydrogen or straight-chain or branched alkyl having up to 4 carbon atoms, R⁵ denotes straight-chain or branched alkyl or alkenyl having up to 4 carbon atoms, which are optionally substituted by cyclopropyl or phenyl, or A has the abovementioned meanings and B and D together form a radical of the formula

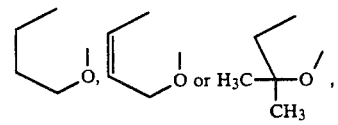

E represents a heterocyclic radical of the formula

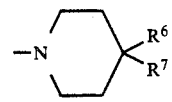

wherein

R⁶ denotes hydrogen, hydroxyl, fluorine, chlorine, phenyl or piperidinyl,

R⁷ denotes straight-chain or branched alkyl having up to 4 carbon atoms, which is optionally substituted by up to 3 identical or different substituents from the group comprising hydroxyl and phenyl, wherein the phenyl ring in turn can be substituted by up to 2 identical or different substituents from the group comprising fluorine, chlorine and trifluoromethyl, or denotes phenyl, which is optionally substituted by up to 3 identical or different substituents from the group comprising fluorine, chlorine, trifluoromethyl, hydroxyl, methyl and methoxy, or denotes a group of the formula —CO—NR⁸R⁹, —COR¹⁰ or —OR¹¹, wherein $R^8$ and $R^9$ are identical or different and denote hydrogen, methyl or ethyl and $R^{10}$ and $R^{11}$ are identical or different and denote phenyl, which is optionally substituted by fluorine, chlorine or trifluoromethyl, and salts thereof, with the proviso that $R^6$ does not denote hydrogen or hydroxyl if $R^7$ represents unsubstituted phenyl.

Processes have also been found for the preparation of the compounds according to the invention of the general formula (I), characterised in that

[A] Compounds of the general formula (II)

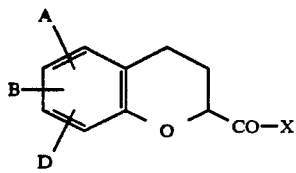
(II)

in which

A, B and D have the abovementioned meaning and

X represents halogen or hydroxyl, are converted, if appropriate after prior activation with carbonyldiimidazole (X-OH), with the cyclic amines of the general formula (III)

H—E    (III)

in which

E has the abovementioned meaning, into the compounds of the general formula (IV)

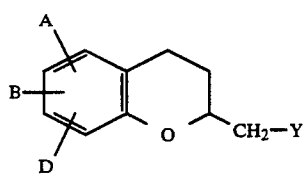
(IV)

in which

A, B, D and E have the abovementioned meaning, in inert solvents in the presence of a base, and the carbonyl group is then reduced to the methylene group with the customary reducing agents in the presence of an inert solvent, or

[B] Compounds of the general formula (V)

(V)

in which

A, B and D have the abovementioned meaning and

Y represents hydroxyl or represents a typical leaving group, such as, for example, rosylate, chloride or mesylate, preferably tosylate, are reacted directly with compounds of the general formula (III) in inert solvents in the presence of a base and if appropriate an auxiliary (catalyst, starter), and in the case where the cyclic amine (E) is substituted, the particular radicals are introduced by customary methods, for example by reduction of nucleophilic substitution, preferably via a Mitsunobu reaction, and if appropriate the substituents A, B and D are varied, likewise by customary methods.

The processes according to the invention can be illustrated by way of example by the following equation:

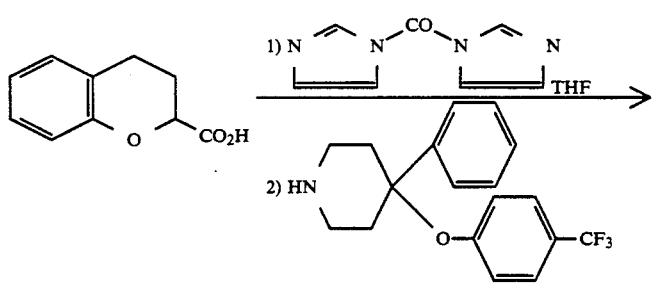
[A]

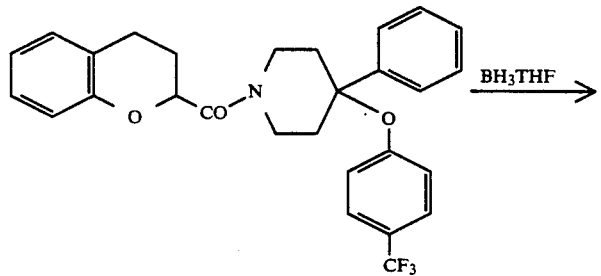

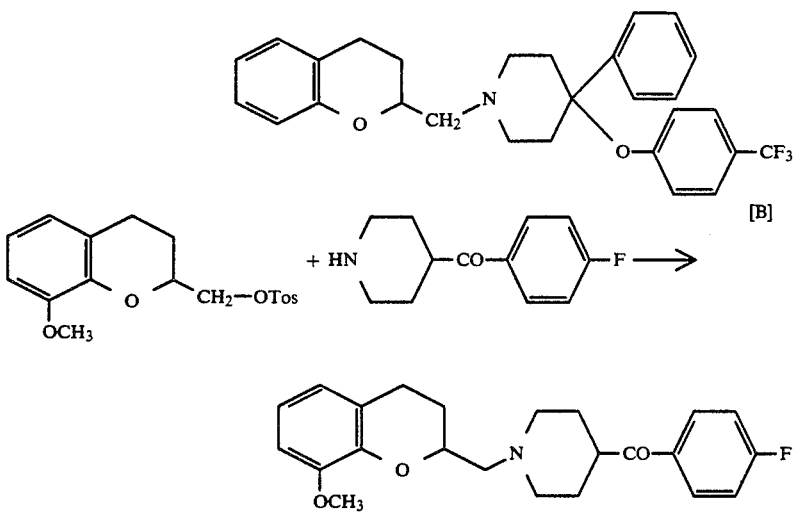

[B]

Suitable solvents for the reaction with the amines of the general formula (III) are the customary solvents which do not change under the reaction conditions. These include, preferably, alcohols, such as methanol, ethanol, propanol or isopropanol, or ethers, such as diethyl ether, dioxane, tetrahydrofuran, glycol dimethyl ether or butyl methyl ether, or ketones, such as acetone or butanone, or amides, such as dimethylformamide or hexamethylphosphoric acid triamide, or dimethyl sulphoxide, acetonitrile or ethyl acetate, or halogenohydrocarbons, such as methylene chloride, chloroform or carbon tetrachloride, or pyridine, picoline or N-methylpiperidine. Mixtures of the solvents mentioned can likewise be used. Methanol, ethanol, propanol, isopropanol and dimethylformamide are preferred.

Suitable bases are the customary inorganic or organic bases. These include, preferably, alkali metal hydroxides, such as, for example, sodium hydroxide or potassium hydroxide, or alkali metal carbonates, such as sodium carbonate or potassium carbonate, or alkali metal alcoholares, such as, for example, sodium methanolate or potassium methanolate, or sodium ethanolate or potassium ethanolate, or organic amines, such as triethylamine, picoline, pyridines or N-methylpiperidine, or amides, such as sodium amide or lithium diisopropylamide. Sodium carbonate, potassium carbonate and pyridine are preferred.

The base is employed in an amount of 0.5 mol to 10 mol, preferably 0.3 mol to 3 mol per mole of the compounds of the general formulae (II) and (V). In the case of pyridine, the base can also be employed as the solvent.

The reaction is in general carried out in a temperature range from 0° C. to 150° C., preferably +20° C. to +110° C.

The reaction can be carried out under normal, increased or reduced pressure (for example 0.5 to 5 bar). It is in general carried out under normal pressure.

The reduction of the cyclic acid amides is carried out with hydrides in inert solvents, or with boranes, diboranes or their complex compounds.

The reactions are preferably carried out with hydrides, such as complex borohydrides or aluminium hydrides, and boranes. Sodium borohydride, lithium aluminium hydride, sodium bis-(2-methoxyethoxy)aluminiumhydride or boranetetrahydrofuran are particularly preferably employed here.

The reaction can be carried out under normal, increased or reduced pressure (for example 0.5 to 5 bar). It is in general carried out under normal pressure.

The reduction is in general carried out in a temperature range from −50° C. up to the particular boiling point of the solvent, preferably from −20° C. to +90° C.

The reductions can in general be carried out by hydrogen in water or in inert organic solvents, such as alcohols, ethers or halogenohydrocarbons, or mixtures thereof, using catalysts such as Raney nickel, palladium, palladium on animal charcoal or platinum, or with hydrides or boranes in inert solvents, if appropriate in the presence of a catalyst.

The reaction is preferably carried out with hydrides, such as complex borohydrides or aluminium hydrides. Sodium borohydride, lithium aluminium hydride or sodium cyanoborohydride are particularly preferably employed here.

Suitable solvents here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric acid triamide or dimethylformamide, or acetic acid. It is also possible to use mixtures of the solvents mentioned.

Proton acids are in general used as catalysts in the reduction with sodium cyanoborohydride. These include, preferably, inorganic acids, such as, for example, hydrochloric acid or sulphuric acid, or organic carboxylic acids which have 1–6 carbon atoms and are optionally substituted by fluorine, chlorine and/or bromine, such as, for example, acetic acid, trifluoroacetic acid, trichloroacetic acid or propionic acid, or sulphonic acids with $C_1$–$C_4$-alkyl radicals or aryl radicals, such as, for example, methanesulphonic acid, ethanesulphonic acid, benzenesulphonic acid or toluenesulphonic acid.

The Mitsunobu reaction in general proceeds in one of the abovementioned non-protic solvents, preferably tetrahydrofuran, in the presence of phosphanes, preferably triphenylphosphane, and ester derivatives of azodicarboxylic acid, preferably diethyl azodicarboxylate, in a temperature range from 0° C. to +50° C., preferably at room temperature under normal pressure (in this context, compare Synthesis 1981,1).

The compounds of the general formula (II) and (V) are known per se or can be prepared by the customary methods [compare DE 3,620,408 A, U.S. Pat. No. 4,957,928 and Farmaco, Ed. Sci. 42 (II), 805–813].

The cyclic amines of the general formula (III) are known, can be prepared by customary methods or are commercially available [compare MSD Book 2, 2846 D; and Beilstein 21 (2) 8].

The compounds of the general formula (IV) are known in some cases, or are new, and in this case can be obtained for example by the abovementioned processes.

The compounds according to the invention can be used as active compounds in medicaments. The substances according to the invention have a particularly high affinity for cerebral 5-hydroxy-tryptamine receptors of the 5-HT$_1$ type. They also have a high affinity for dopamine receptors of the D$_2$ type.

The substances according to the invention surprisingly exhibit an advantageous action on the central nervous system, and can be used for therapeutic treatment of humans and animals.

The compounds described in the present invention are thus active compounds for combating diseases which are characterised by disturbances in the serotoninergic and dopaminergic system, in particular involving receptors which have a high affinity for 5-hydroxytryptamine (5-HT$_1$ type) and/or for dopamine (D$_2$ type). They are therefore suitable for the treatment of illnesses of the central nervous system, such as states of anxiety, stress and depression, and sexual dysfunctions and sleep disturbances of central nervous origin, and for regulating pathological disturbances in the intake of food, luxury substances and addictlye agents. They are moreover suitable for the deficiencies elimination of cognitive, for improving learning and memory performance and for the treatment of Alzheimer's disease. They are also suitable for the treatment of psychoses (for example schizophrenia or mania). Compared with known neuroleptics, they have a lower side-effects potential.

Furthermore these active compounds are also suitable for modulating the cardiovascular system. They also intervene in the regulation of the cerebral circulation, and are thus effective agents for combating migraine.

They are also suitable for prophylaxis of and combating the consequences of cerebral infarctions (Apoplexia cerebri), such as apoplexy and cerebral ischaemias. The compounds moreover can be used for the treatment of acute cranio-cerebral trauma. The compounds according to the invention can likewise be employed for combating attacks of pain.

Affinity for the 5-HT$_1$ receptor

The high affinity of the compounds according to the invention for 5-hydroxytryptamine receptors of the subtype 1 is shown by way of example in Table [A]. The values stated are data which were determined from receptor-bonding studies using calf hippocampus membrane preparations. $^3$H-Serotonin was used as the radioactively labelled ligand for this purpose.

TABLE [A]

| Compound of Example | K$_i$ (nmol/l) |
| --- | --- |
| 1 | 22 |

TABLE [A]-continued

| Compound of Example | K$_i$ (nmol/l) |
| --- | --- |
| 4 | 76 |

Affinity for the 5-HT$_{1A}$ receptor

[W. U. Dompert et al., Naunyn-Schmiedeberg's Arch. Pharmacol. (1985), 328, 467–470].

The bonding of $^3$H-ipsapirone to 5-HT$_{1A}$ receptors in calf hippocampus membranes is measured in this test. It was found that the compounds according to the invention compete with the radioligands for the bonding and inhibit these.

TABLE [B]

| Compound of Example | K$_i$ (nmol/l) |
| --- | --- |
| 5 | 9.9 |
| 9 | 6 |

Dopamine D$_2$ receptor test

This test is carried out in accordance with the following literature reference: Imafuku J. (1987), Brain Research 402; 331–338.

The bonding of the selective D$_2$ receptor antagonist $^3$H-sulpiride to membranes from the striatum of the rat is measured here. Compounds which bond to dopamine D$_2$ receptors inhibit the bonding of $^3$H-sulpiride as a function of the concentration. IC$_{50}$ values are determined from the displacement curves, and the inhibition constants K$_i$ are calculated from these.

TABLE [C]

| Compound of Example | K$_i$ (nmol/l) |
| --- | --- |
| 4 | 2.5 |
| 8 | 0.9 |
| 10 | 2.3 |

The present invention also includes pharmaceutical formulations which contain, in addition to inert, non-toxic, pharmaceutically suitable auxiliaries and excipients, one or more compounds of the general formula (I), or which consist of one or more active compounds of the formula (I), and to processes for the preparation of these formulations.

The active compounds of the formula (I) should be present in these formulations in a concentration of 0.1 to 99.5% by weight, preferably 0.5 to 95% by weight of the total mixture.

In addition to the active compounds of the formula (I), the pharmaceutical formulations can also contain other pharmaceutical active compounds.

The abovementioned pharmaceutical formulations can be prepared in the customary manner by known methods, for example with the auxiliary or excipient substance or substances.

In general, it has proved advantageous to administer the active compound or compounds of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, it may be advantageous, where appropriate, to deviate from the amounts mentioned, and in particular to do so as a function of the nature and body weight of the subject treated, of the behaviour of the individual towards the medicament, of the nature and severity of the illness, of the nature of the formulation and administration, and of the time or interval at which administration takes place.

The particular $R_f$ values stated were determined—unless noted otherwise—by thin layer chromatography on silica gel (aluminium foil, silica gel 60 F 254, E. Merck). The substance spots were visualised by viewing under UV light and/or by spraying with 1% strength potassium permanganate solution.

The flash chromatography was carried out on silica gel 60, 0.040–0.064 mm, E. Merck (see Still et al., J. Org. Chem. 43, 2923, 1978; for simpler separation problems, see Aldrichimica Acta 18, 25, 1985). Elution with solvent gradients means: starting with the pure, non-polar solvent mixture component, the polar mobile phase component is admixed to an increasing extent, until the desired product is eluted (thin layer chromatography control).

In the case of all the products, the solvent was distilled off under a final pressure of about 0.1 mm Hg. Salts were kept under this pressure overnight over potassium hydroxide and/or phosphorus pentoxide.

STARTING COMPOUNDS

EXAMPLE I

2-Hydroxymethyl-8methoxy-chroman

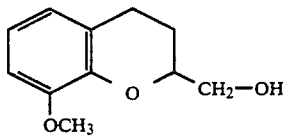

59.0 g (0.25 mol) of ethyl 8-methoxy-chroman-2-carboxylate in 525 ml of anhydrous tetrahydrofuran are added dropwise to a suspension of 9.5 g (0.25 mol) of lithium aluminium hydride in 525 ml of anhydrous diethyl ether at 20° C. in the course of 1 hour, while stirring. The mixture is stirred overnight, and 9.5 ml of water, 9.5 ml of 15% strength sodium hydroxide solution and 28.4 ml of water are then added dropwise in succession, while cooling. The organic phase is decanted and evaporated. The residue is recrystallised twice from methylene chloride/petroleum ether.

Yield: 38.0 g (87%)

Melting point: 57°–58° C.

EXAMPLE II (2R)-2-Hydroxymethyl-chroman

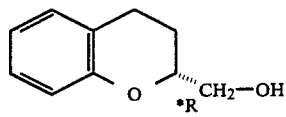

164 ml of a 1 M borane solution in tetrahydrofuran are added dropwise to a solution of 22.1 g (0.124 mol) of (2R)-chroman-2-carboxylic acid (ee =98.3%) in 210 ml of anhydrous tetrahydrofuran at an internal temperature of 0° C. under argon in the course of 30 minutes. The cooling is removed and the mixture is subsequently stirred for 4 hours. During this procedure, the internal temperature rises to 34° C. 46 ml of a 1/1 mixture of tetrahydrofuran and water are then added dropwise, while cooling with ice. After addition of 40.7 g of anhydrous potassium carbonate and vigorous stirring, the tetrahydrofuran solution is decanted and concentrated under a waterpump vacuum. Flash distillation gives 18.8 g of colourless 2R-hydroxymethylchroman of boiling point 77°–78° C./0.15 mbar. ee>99%.

EXAMPLE III (2S)-2-Hydroxymethyl-chroman

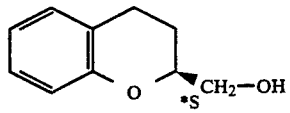

The title compound is prepared from (2S)-2-chroman-2-carboxylic acid analogously to the instructions of Example I.

ee>99%

Boiling point: 79°–81° C./0.15 mbar

EXAMPLE IV (2R)-2-Tosyloxymethyl-chroman

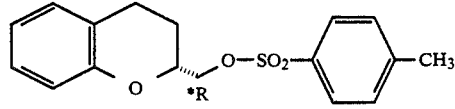

15.63 g (0.082 mol) of 4-toluenesulphonyl chloride are added in portions to 12.8 g (0.078 mol) of (2R)-2-hydroxymethylchroman (Example II) in 50 ml of anhydrous pyridine, while stirring and cooling with ice. After the mixture has been left to stand overnight, it is introduced into ice-water and extracted with diethyl ether. The ether phase is washed twice with 5% strength ice-cold hydrochloric acid and then with saturated sodiumchloride solution, dried over anhydrous sodium sulphate and evaporated under a waterpump vacuum. 22.4 g of uniform 4-toluenesulphonic acid ester of 2R-2-hydroxymethylchroman are obtained.

$R_f$=0.6 (toluene/ethyl acetate 3:1) oil

Melting point: 62°–65° C. (petroleum ether/methylene chloride); $[\alpha]_D = -51.1°$ (C=1, chloroform)

EXAMPLE V (2S)-2-Tosyloxymethyl-chroman

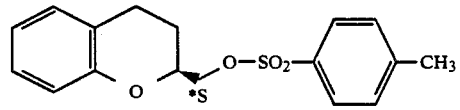

The title compound is prepared from Example III analogously to the instructions of Example III. $R_f$=0.6 (toluene/ethyl acetate 3:1) oil

EXAMPLE VI

8-Methoxy-2-tosyloxymethyl-chroman

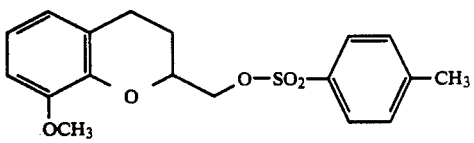

Melting point: 115-117 (from methylene chloride)

EXAMPLE VII

N-(3,4-Dihydro-2H-1-benzopyran-2-carbonyl-4-phenyl-4-(4-trifluoromethyl phenoxy)piperidine

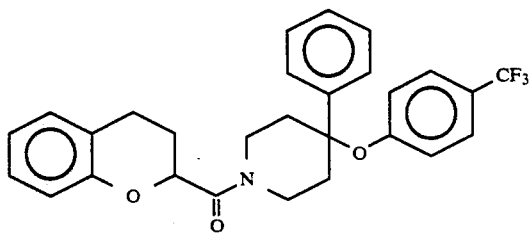

A solution of 0.89 g (5.5 mmol) of 1,1-carbonyldiimidazole and 11 ml of dry tetrahydrofuran is added dropwise to a solution of 0.89 g (5.0 mmol) of 3,4-dihydro-2H-1-benzopyran-2-carboxylic acid and 5.5 ml of dry tetrahydrofuran at 20°-25° C. in the course of 1 hour. The reaction solution is then stirred at room temperature for a further 2 hours. A solution of 1.93 g (6.0 mmol) of 4-phenyl-4-(4-trifluoromethyl-phenoxy)-piperidine is then added dropwise at 25° C. in the course of 1 hour. After 18 hours at room temperature, the reaction solution is stirred into a mixture of 220 ml of 5% strength sodium chloride solution, 13 ml of 1 molar hydrochloric acid and 110 ml of toluene for working up. The aqueous phase is extracted once more with 55 ml of toluene. The combined organic phases are then washed with 55 ml each of 0.1 molar hydrochloric acid, followed by 1% strength sodium bicarbonate solution and then water. The organic phase is dried with sodium sulphate and concentrated to dryness.

The residue is dissolved in 9 ml of toluene and crystallised by dropwise addition of 45 ml of petroleum spirit. After cooling to 10°-15° C., the crystals were filtered off with suction and dried at 50° C. in vacuo.

Yield: 2.0 g = 83% of theory
Melting point: 148°-149° C.

Preparation Examples

EXAMPLE 1

2-[4-( 4-Chlorophenyl )-4-hydroxy-piperidin-1-yl ]methyl-8-methoxy-chroman hydrochloride

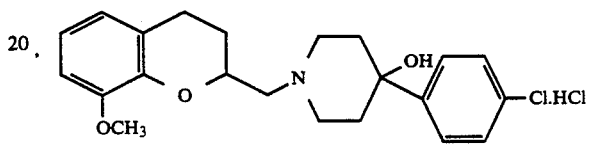

A mixture of 2.4 g (6.9 retool) of the compound from Example VI, 0.5 g ( 4.8 mmol) of anhydrous sodium carbonate and 1.5 g (6.9 retool) of 4-hydroxy-4-(4-chlorophenyl)piperidine in 15 ml of dimethylformamide is stirred at 110° C. for 6 hours and then poured onto ice. Extraction with ethyl acetate, washing of the organic phase and drying and evaporation of the organic phase under a waterpump vacuum gives the crude product (3.2 g), which is purified by chromatography (200 g of silica gel, toluene/ethyl acetate 1:1).

Melting point ° C=86–88 from methylene chloride/ether. The hydrochloride accessible from this compound with ethereal hydrochloric acid has a melting point of 193°-198° C. (capillary).

The examples listed in Table 1 were prepared analogously to the instructions of Example 1.

TABLE 1

![structure with B on ring, A on ring, O-CH2-E]

| Example No. | A | B | E | Melting point °C. |
|---|---|---|---|---|
| 2 | —OCH₃ | H | —N(piperidine)-H, CO-C₆H₄-F | 107 (free base) |
| 3 | H | H | —N(piperidine)-CH₂—C₆H₅ | 186–188 (hydrochloride) |
| 4 | H | H | —N(piperidine)-OH, C₆H₄-Cl | 204–211 (hydrochloride) |

TABLE 1-continued

Structure: chroman with substituents B and A on benzene ring, and CH₂—E on the oxygen-bearing carbon.

| Example No. | A | B | E | Melting point °C. |
|---|---|---|---|---|
| 5 | —OCH₃ | H | —N(piperidine with 4,4-diphenyl: C₆H₅, C₆H₅) | 243 (hydrochloride) |
| 6 | H | H | —N(piperidine-4-yl with 4-piperidino and 4-CO—NH₂) | 125–127 (free base) |
| 7 | —OCH₃ | H | —N(piperidine-4-yl with 4-piperidino and 4-CONH₂) | 140–141 (free base) |
| 8 | H | H | —N(4-methylpiperidin-4-ol with 4-(3-CF₃-4-Cl-phenyl)) | 232–235 (hydrochloride) |
| 9 | —OCH₃ | H | —N(4-methylpiperidin-4-ol with 4-(3-CF₃-phenyl)) | 218–221 (hydrochloride) |
| 10 | H | H | —N(4-methylpiperidin-4-ol with 4-(3-CF₃-phenyl)) | 202–205 (hydrochloride) |
| 11 | —OCH₃ | H | —N(4-methylpiperidin-4-ol with 4-(3-CF₃-4-Cl-phenyl)) | 231–233 (hydrochloride) |

EXAMPLE 12

2-{[4-(4-Trifluorophenoxy)-4-phenyl]piperidin-1-yl}methyl-chroman hydrochloride

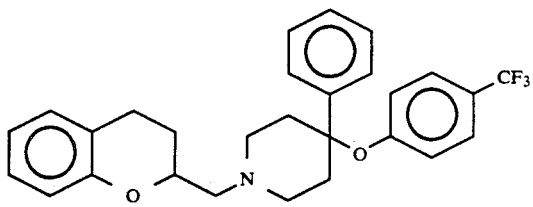

1.90 g (3.9 mmol) of the compound from Example VII are dissolved in 29 ml of dry tetrahydrofuran under argon, and 19.5 ml of a 1 molar solution of boran-tetrahydrofuran complex are added dropwise at 25° C. in the course of 30 minutes. The reaction solution is then heated at 50° C. for 1½ hours. 7.8 ml of a 1 molar hydrochloric acid are then added dropwise at 50° C. in the course of 15 minutes, and the mixture is left at 50° C. for a further hour. After cooling, the reaction solution is stirred into a mixture of 250 ml of 5% strength sodium chloride solution and 125 ml of toluene. The aqueous phase is extracted once more with 60 ml of toluene. The combined organic phases are concentrated down to 50 ml, in order to remove the tetrahydrofuran, and are topped up again with toluene. The organic phase is then washed neutral with 50 ml each of 0.5% strength sodium bicarbonate solution and water, dried over sodium sulphate and concentrated to dryness. An oily crude product, in the form of the base, remains as the residue. The crude product is purified by column chromatography on silica gel using cyclohexane/ethyl acetate 30:70.

Yield: 1.46 g = 80% of theory 1.43 g of the base (3.0 mmol) are dissolved in 70 ml of diethyl ether, and the hydrochloride is precipitated by dropwise addition of 15 ml of ethereal hydrogen chloride solution (3.3 mmol). The suspension is then stirred for a further hour, and the crystals are filtered off with suction and dried at 50° C. in vacuo (1.45 g).

Yield: 1.37 g = 86% of theory (hydrochloride)
Thin layer chromatography: $R_f = 0.58$
Melting point: ° C = 172–173

EXAMPLE 13

N-Methyl-( 3,4-dihydro-2H-8-methoxy-1-benzopyran-2-yl )-4-phenyl-4- (4-trifluoromethylphenoxy)-piperidine

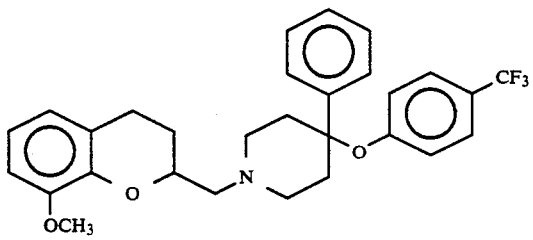

The title compound is prepared analogously to Example 12 from 2.14 g (4.2 retool) of N-carbonyl-(3,4-dihydro-2H-8-methoxy-1-benzopyran-2-yl )-4-phenyl-4-( 4-trifluoromethylphenoxy)-piperidine.

Yield: 1.53 g = 73% of theory (base)
Thin layer chromatography: $R_f = 0.35$

We claim:

1. Piperidylmethyl-substituted chroman derivatives of the general formula (I)

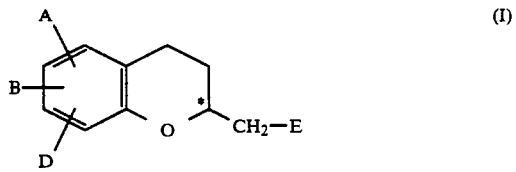

in which

A, B and D are identical or different and represent hydrogen, halogen, cyano, azido, nitro, difluoromethyl, trifluoromethyl, difluoromethoxy, trifluoromethoxy, hydroxyl or carboxyl, or represent straight-chain or branched alkyl, alkenyl, acyl or alkoxycarbonyl having in each case up to 8 carbon atoms, or represent a group of the formula $-NR^1R^2$, $-NR^3-L-R^4$ or $-OR^5$, wherein $R^1$, $R^2$ and $R^3$ are identical or different and denote hydrogen, straight-chain or branched alkyl having up to 8 carbon atoms, phenyl or benzyl, L denotes the $-CO-$ or $-SO_2-$ group, $R^4$ denotes straight-chain or branched alkyl having up to 8 carbon atoms or benzyl, or phenyl, which is optionally substituted by halogen, hydroxyl, nitro, cyano, trifluoromethyl, trifluoromethoxy or by straight-chain or branched alkyl or alkoxy having up to 6 carbon atoms, $R^5$ denotes straight-chain or branched alkyl or alkenyl having in each case up to 8 carbon atoms, which are optionally substituted by cycloalkyl having 3 to 6 carbon atoms or phenyl, E represents a heterocyclic radical of the formula

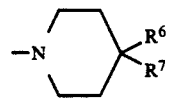

wherein $R^6$ denotes hydrogen, hydroxyl, halogen, phenyl or piperidinyl, $R^7$ denotes straight-chain or branched alkyl having up to 8 carbon atoms, which is optionally substituted by up to 3 identical or different substituents from the group consisting of hydroxy, straight-chain or branched alkoxy having up to 6 carbon atoms and phenyl, wherein the phenyl ring in turn can be substituted by up to 3 identical or different substituents from the group consisting of halogen, trifluoromethyl, trifluoromethoxy and cyano; denotes phenyl, which is optionally substituted by up to 3 identical or different substituents from the group consisting of halogen, trifluoromethyl, trifluoromethoxy, cyano, nitro, hydroxyl and straight-chain or branched alkyl and alkoxy having in each case up to 6 carbon atoms; or denotes a group selected from the formula $-CO-NR^8R^9$, $-CO-R^{10}$ or $-OR^{11}$; wherein $R^8$ and $R^9$ are identical or different and denote hydrogen, straight-chain or branched alkyl having up to 6 carbon atoms or phenyl, and $R^{10}$ and $R^{11}$ are identical or different and denote phenyl, which is optionally substituted by up to 2 identical or different substituents from the group consisting of halogen, cyano, nitro, trifluoromethyl and trifluoromethoxy, and salts thereof, with the proviso that $R^6$ does not denote hydrogen or hydroxyl if $R^7$ represents unsubstituted phenyl, and with the further proviso that if $R^7$ denotes $CONR^8R^9$ hydroxylalkyl or alkoxyalkyl then $R^6$ does not denote hydrogen.

2. Piperidylmethyl-substituted chroman derivatives according to claim 1, wherein A, B and D are identical or different and represent hydrogen, fluorine, chlorine bromine, cyano, trifluoromethyl, difluoromethoxy, trifluoromethoxy or hydroxyl, or represent straight-chain or branched alkyl, alkenyl, acyl or alkoxycarbonyl having in each case up to 6 carbon atoms, or represent a group of the formula $-NR^1R^2$, $-NR^3-L-R^4$ or $-OR^5$, wherein $R^1$, $R^2$ and $R^3$ are identical or different and denote hydrogen or straight-chain or branched alkyl having up to 6 carbon atoms, L denotes the $-CO-$ or $-SO_2-$ group, $R^4$ denotes straight-chain or branched alkyl having up to 6 carbon atoms or benzyl, or denotes phenyl, which is optionally substituted by fluorine, chlorine, bromine, trifluoromethyl, trifluoromethoxy or hydroxyl, or by straight-chain or branched alkyl or alkoxy having up to 4 carbon atoms, $R^5$ denotes straight-chain or branched alkyl or alkenyl having up to 6 carbon atoms, which are optionally substituted by cyclopropyl, cyclopentyl, cyclohexyl or phenyl, E is

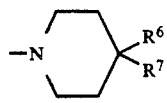

wherein

R⁶ denotes hydrogen, hydroxyl, fluorine, chlorine, bromine, phenyl or piperidinyl, R⁷ denotes straight-chain or branched alkyl having up to 6 carbon atoms, which is optionally substituted by up to 3 identical or different substituents from the group consisting of hydroxyl, straight-chain or branched alkoxy having up to 4 carbon atoms and phenyl, wherein the phenyl ring in turn can be substituted by up to 3 identical or different substituents from the group consisting of fluorine, chlorine, bromine and trifluoromethyl, or denotes phenyl, which is optionally substituted by up to 3 identical or different substituents from the group consisting of fluorine, chlorine, bromine, trifluoromethyl, hydroxyl and straight-chain or branched alkyl and alkoxy having in each case up to 4 carbon atoms, or denotes a group of the formula —CO—NR⁸R⁹, —COR¹⁰ or —OR¹¹, wherein R⁸ and R⁹ are identical or different and denote hydrogen or straight-chain or branched alkyl having up to 4 carbon atoms, and R¹⁰ and R¹¹ are identical or different and denote phenyl, which is optionally substituted by up to 2 identical or different substituents from the group consisting of fluorine, chlorine, bromine and trifluoromethyl, and salts thereof, with the proviso that R⁶ does not denote hydrogen or hydroxyl if R⁷ represents unsubstituted phenyl, and with the further proviso that if R⁷ denotes CONR⁸R⁹ hydroxyalkyl or alkoxyalkyl then R⁶ does not denote hydrogen.

3. Piperidylmethyl-substituted chroman derivatives according to claim 1, wherein A, B and D are identical or different and represent hydrogen, fluorine, chlorine, bromine, cyano, trifluoromethyl, trifluoromethoxy or hydroxyl, or represent straight-chain or branched alkyl or alkenyl having in each case up to 4 carbon atoms, or represent a group of the formula —NR¹R² or —OR⁵, wherein R¹ and R² are identical or different and denote hydrogen or straight-chain or branched alkyl having up to 4 carbon atoms, R⁵ denotes straight-chain or branched alkyl or alkenyl having up to 4 carbon atoms, which are optionally substituted by cyclopropyl or phenyl, E is

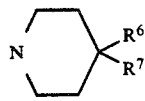

wherein

R⁶ denotes hydrogen, hydroxyl, fluorine, chlorine, phenyl or piperidinyl,

R⁷ denotes straight-chain or branched alkyl having up to 4 carbon atoms, which is optionally substituted by up to 3 identical or different substituents from the group consisting of hydroxyl and phenyl, wherein the phenyl ring in turn can be substituted by up to 2 identical or different substituents from the group consisting of fluorine, chlorine and trifluoromethyl, or denotes phenyl, which is optionally substituted by up to 3 identical or different substituents from the group consisting of fluorine, chlorine, trifluoromethyl, hydroxyl, methyl and methoxy, or denotes a group of the formula —CO—NR⁸R⁹, —COR¹⁰ or —OR¹¹, wherein R⁸ and R⁹ are identical or different and denote hydrogen, methyl or ethyl and R¹⁰ and R¹¹ are identical or different and denote phenyl, which is optionally substituted by fluorine, chlorine or trifluoromethyl, and salts thereof, with the proviso that R⁶ does not denote hydrogen or hydroxyl if R⁷ represents unsubstituted phenyl, and with the further proviso that if R⁷ denotes CONR⁸R⁹, hydroxyalkyl or alkoxyalkyl, then R⁶ does not denote hydrogen.

4. A compound according to claim 1, wherein such compound is 2-[4-(4-chlorophenyl)-4-hydroxy-piperidin-1-yl]methyl-8-methoxy-chroman of the formula

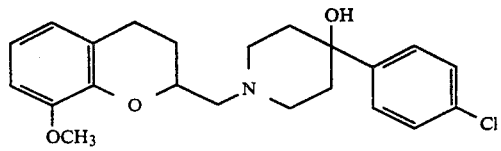

or a salt thereof.

5. A compound according to claim 1, wherein such compound is 2-[4-(4-fluorobenzoyl)-piperidin-1-yl]methyl-8-methoxy-chroman of the formula

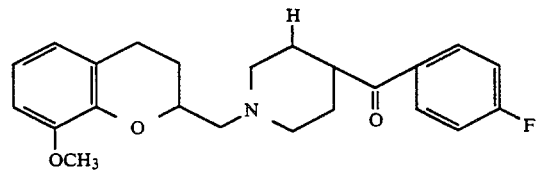

or a salt thereof.

6. A compound according to claim 1 wherein such compounds is 2-[4-(3-trifluoromethylphenyl)-4-hydroxy-piperidin-1-yl]methyl-chroman of the formula

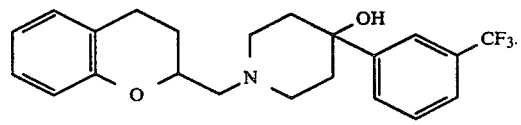

or a salt thereof.

7. A compound according to claim 1 wherein such compound is 2-[4-(-chloro-3-trifluoro-methyl-phenyl)-4-hydroxy-piperidin-1-yl]methyl-8-methoxy-chroman of the formula

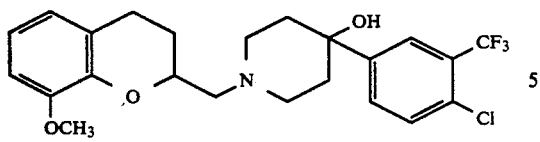

or a salt thereof.

8. A composition for the treatment of diseases which are characterized by disturbances of the serotoninergic and the dopaminergic system comprising an amount effective therefor of a compound or salt thereof according to claim 1 and a pharmacologically acceptable diluent.

9. A method of treating diseases which are characterized by disturbances of the serotoninergic and the dopaminergic system in a patient in need thereof which comprises administering to such patient an amount effective therefor of a compound or salt thereof according to claim 1.

10. Piperidylmethyl-substituted chroman derivatives according to claim 1, wherein
$R^6$ denotes hydroxy, halogen, phenyl or piperidinyl, and
$R^7$ denotes straight-chain or branched alkyl having up to 8 carbon atoms, which is optionally substituted by up to 3 identical or different substituents from the group consisting of hydroxy, straight-chain or branched alkoxy having up to 6 carbon atoms and phenyl, wherein the phenyl ring in turn can be substituted by up to 3 identical or different substituents from the group consisting of halogen, trifluoromethyl, trifluoromethoxy and cyano, or denotes phenyl, which is optionally substituted by up to 3 identical or different substituents from the group consisting of halogen, trifluoromethyl, trifluoromethoxy, cyano, nitro, hydroxyl and straight-chain or branched alkyl and alkoxy having in each case up to 6 carbon atoms, or denotes a group of the formula $-CO-NR^8R^9$, $-CO-R^{10}$ or $-OR^{11}$, wherein
$R^8$ and $R^9$ are identical or different and denote hydrogen, straight-chain or branched alkyl having up to 6 carbon atoms or phenyl, and
$R^{10}$ and $R^{11}$ are identical or different and denote phenyl, which is optionally substituted by up to 2 identical or different substituents from the group consisting of halogen, cyano, nitro, trifluoromethyl and trifluoromethoxy.

11. Piperidylmethyl-substituted chroman derivatives according to claim 1, wherein
$R^7$ denotes straight-chain or branched alkyl having up to 8 carbon atoms, which is optionally substituted by up to 3 identical or different substituents from the group consisting of hydroxy, straight-chain or branched alkoxy having up to 6 carbon atoms and phenyl, wherein the phenyl ring in turn can be substituted by up to 3 identical or different substituents from the group consisting of halogen, trifluoromethyl, trifluoromethoxy and cyano, or denotes phenyl, which is optionally substituted by up to 3 identical or different substituents from the group consisting of halogen, trifluoromethyl, trifluoromethoxy, cyano, nitro, hydroxyl and straight-chain or branched alkyl and alkoxy having in each case up to 6 carbon atoms.

12. A piperidylmethyl-substituted chroman derivative according to claim 1 of the formula

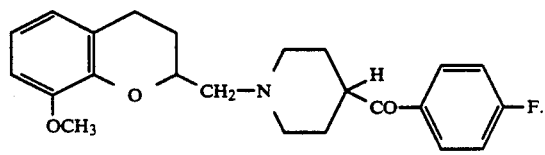

13. A piperidylmethyl-substituted chroman derivative according to claim 1 of the formula

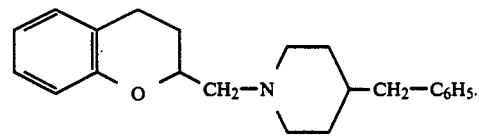

14. A piperidylmethyl-substituted chroman derivative according to claim 1 of the formula

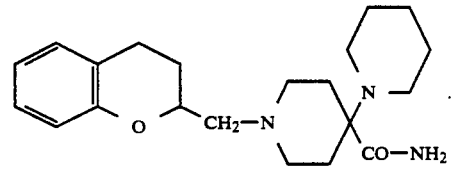

15. A piperidylmethyl-substituted chroman derivative according to claim 1 of the formula

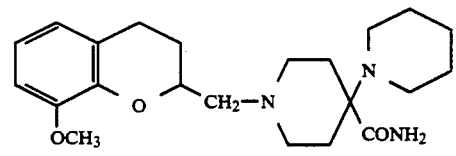

* * * * *

UNITED STATES PATENT AND TRADEMARK OFFICE
CERTIFICATE OF CORRECTION

PATENT NO.   : 5,326,771
DATED        : July 5, 1994
INVENTOR(S)  : Hans-Georg Heine et al.

It is certified that error appears in the above-identified patent and that said Letters Patent is hereby corrected as shown below:

Title page,
OTHER PUBLICATIONS, insert the reference "Beilstein 21 (2) 8"
OTHER PUBLICATIONS, insert the reference "MSD Book 2, 2846D"

Signed and Sealed this

Eighteenth Day of December, 2001

*Attest:*

*Attesting Officer*

JAMES E. ROGAN
*Director of the United States Patent and Trademark Office*